(12) United States Patent
Johnson

(10) Patent No.: US 10,136,962 B2
(45) Date of Patent: Nov. 27, 2018

(54) MULTI-PLANAR PRE-CURVED ROTARY ENDODONTIC FILE

(71) Applicant: William B. Johnson, Tulsa, OK (US)

(72) Inventor: William B. Johnson, Tulsa, OK (US)

(73) Assignee: Dentsply Sirona, Inc., York, PA (US)

( * ) Notice: Subject to any disclaimer, the term of this patent is extended or adjusted under 35 U.S.C. 154(b) by 394 days.

(21) Appl. No.: 14/790,813

(22) Filed: Jul. 2, 2015

(65) Prior Publication Data

US 2015/0359608 A1 Dec. 17, 2015

Related U.S. Application Data

(63) Continuation of application No. 13/354,699, filed on Jan. 20, 2012, now Pat. No. 9,078,722.

(51) Int. Cl.
*A61C 5/42* (2017.01)
*A61C 5/02* (2006.01)

(52) U.S. Cl.
CPC ............... *A61C 5/023* (2013.01); *A61C 5/42* (2017.02)

(58) Field of Classification Search
CPC .................................. A61C 5/023; A61C 5/42
USPC .......................... 433/102, 165; 408/199-230
See application file for complete search history.

(56) References Cited

U.S. PATENT DOCUMENTS

| 4,536,156 A | 8/1985 | Cattin |
| 4,889,487 A | 12/1989 | Lovaas |
| 5,197,880 A * | 3/1993 | Lovaas ............... A61C 5/42 433/102 |
| 5,752,825 A * | 5/1998 | Buchanan ............. A61C 5/42 433/102 |
| 5,842,861 A | 12/1998 | Buchanan |
| 2009/0176188 A1 | 7/2009 | Tobis et al. |
| 2010/0233648 A1 | 9/2010 | McSpadden et al. |
| 2011/0217673 A1 | 9/2011 | Scianamblo |

* cited by examiner

*Primary Examiner* — Yogesh Patel
(74) *Attorney, Agent, or Firm* — Gable Gotwals

(57) ABSTRACT

An improved rotary endodontic file includes a multi-planar pre-curved apical portion having a first and a second curvature. The pre-curved apical portion begins at about one-third to one-quarter of the working length as measured from the tip end of the endodontic instrument. The first and second curvature permit the file to continually search and engage the walls of a tooth root canal in a forced inside-forced outside manner. As the file works its way down, it breaks free of any ledges encountered, probes lateral- and delta-type openings, and does not allow the file to stray from the curvature of the canal.

17 Claims, 4 Drawing Sheets

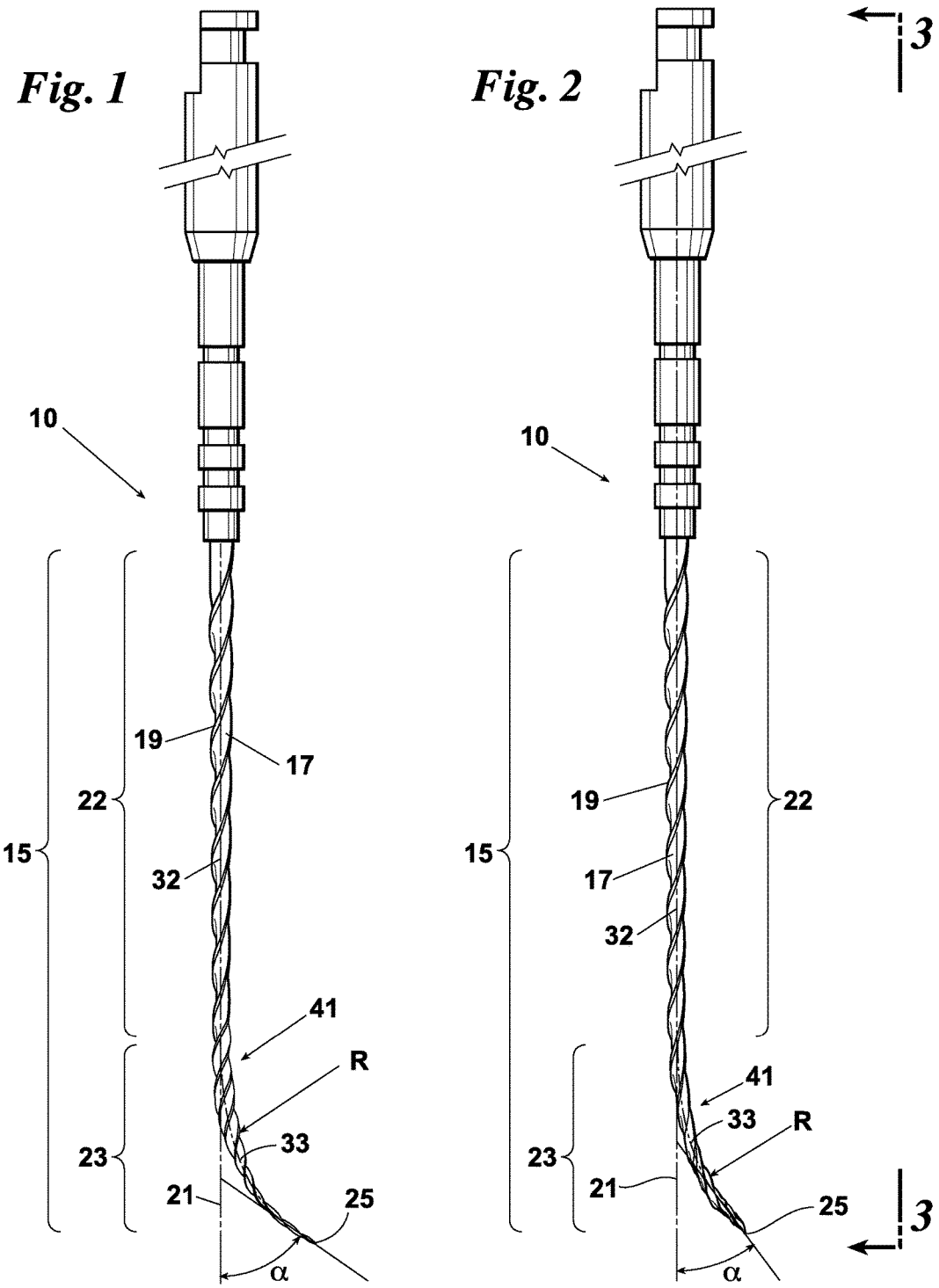

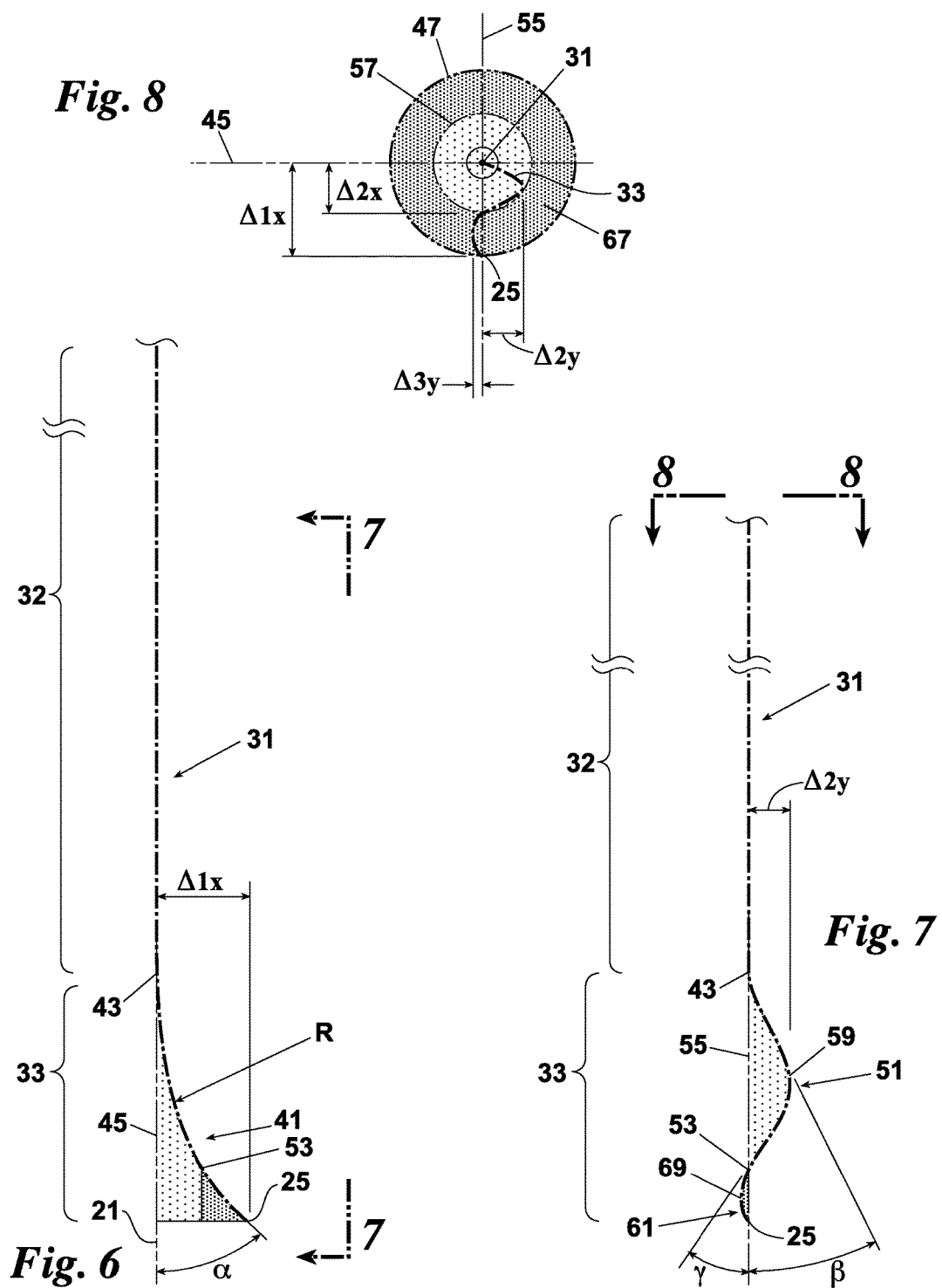

MULTI-PLANAR PRE-CURVED ROTARY ENDODONTIC FILE

REFERENCE TO PENDING APPLICATIONS

This application is a continuation application of U.S. patent application Ser. No. 13/354,699, filed Jan. 20, 2012, the contents of which are hereby incorporated by reference in their entirety.

BACKGROUND OF THE INVENTION

This invention generally relates to endodontic files designed to be used in a rotary hand piece and whose working portion is made of a shape-memory material such as nickel-titanium alloy. More particularly, this invention relates to a pre-curved rotary endodontic file.

Endodontic files intended for use as manual hand files and made out of stainless steel are almost always pre-curved. However, this type of file could not be used in a hand piece because the file would either cut into the root canal wall or break. When rotated in a direction opposite the cutting direction, the file would tend to deform and straighten.

Endodontic files intended for use in a rotary hand piece and made out of a shape memory material such as nickel-titanium alloy do not make use of a pre-curvature. This type of file is designed to be "true" or straight along its entire active or working length relative to the longitudinal axis of the file. The shape-memory characteristic of the file allows it to combine high strength with high flexibility, allowing the file to traverse the curves of a tooth root canal. However, the file continually wants to straighten itself as it traverses those curves and therefore always urges the working portion of the file against the outside curvature of the root canal wall at the expense of the inside curvature. Torsion forces experienced by the file, as well as friction and heat generated by the file, increase as the amount of surface area of the working length of the file contacts the root canal wall. Additionally, because the curvature of the root canal tends to be irregular, the file can encounter a ledge and bind up or cut into the wall, deviate from the curve, and begin to make its own path. Short radius curvatures tend to more problematic with respect to the above than are longer radius curvatures.

Shape-memory eliminated the breakage problems experienced by stainless steel files, and stainless steel files, because they were not flexible, had to be pre-curved. (However, the pre-curved stainless steel files tended to irreversibly straightened when becoming compressed as they traversed straight portions of the root canal.) To intentionally form a curve in a shape-memory endodontic file runs counter to the very reason that a shape-memory material is preferred for use in the first place. However, U.S. Pat. No. 5,842,861 discloses a set of files made from shape-memory material and having a pre-curvature or "hook" in the last one-third of the file. The hook at the end "makes it easier to direct the file down into the apical region of the root canal, particularly where the root is rather tortuously curved or twisted." Each pre-curved file in the set of files can have a different degree of curvature so that a desired shape of the apical region of the root canal can be achieved.

SUMMARY OF THE INVENTION

An improved rotary endodontic instrument or file made according to this invention has a working length made of a shape memory material but includes a pre-curved apical portion having more than one curve. The pre-curved apical portion begins at about one-third to one-quarter of the working length as measured from the tip end of the endodontic instrument. Two or more curvatures are provided in the apical portion, with at least two of the curves lying in a different plane.

Objects of this invention are to provide an improved rotary endodontic file which continually searches the walls of a tooth root canal and, as it works its way down into the canal, dramatically reduces the torque exerted on the file while at the same time maintaining cutting and scraping efficiency, searches the curvature of the canal in addition to lateral- and delta-type openings in the wall of the canal, breaks free of any ledges encountered, and does not allow the file to stray from the curvature of the canal and create new (undesired) openings.

BRIEF DESCRIPTION OF THE DRAWINGS

FIG. 1 is a view of a pre-curved rotary endodontic file made according to this invention and having a first curvature of between 60° to 75° along the apical portion of the file (that is, starting at about the last one-third to one-quarter of the working length).

FIG. 2 is a view of another preferred embodiment of a pre-curved rotary endodontic file made according to this invention. The file has a first pre-curvature in a range of about 30° to 45° along the apical portion of the file.

FIG. 6 is a view of the longitudinal centerline of a file made according to this invention relative to the X plane.

FIG. 7 is a view of the longitudinal centerline of the file of FIG. 6 taken along section line 7-7 of FIG. 6 (relative to the Y plane).

FIG. 8 is a top view of the longitudinal centerline of the file of FIG. 6 taken along section line 8-8 of FIG. 7.

ELEMENTS AND ELEMENT NUMBERING USED IN THE DRAWINGS

Figure 3:
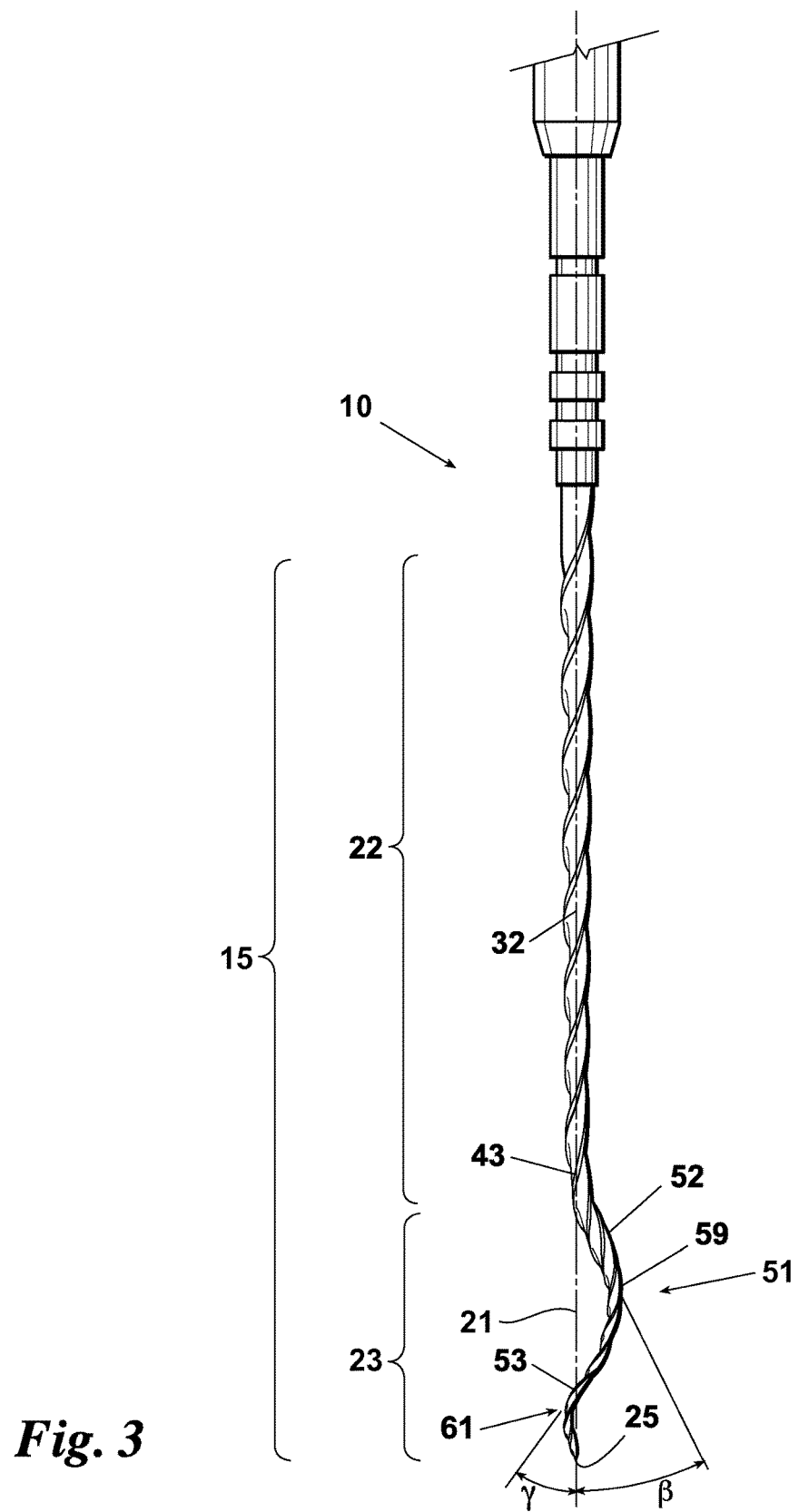
FIG. 3 is a view of the file of FIG. 2 taken along section line 3-3 of FIG. 2. The file includes a first curvature in a range of about 30° to 45° (and could be as high as 75° as shown in FIG. 1) and a second pre-curved portion lying in a plane located about 90° relative to a plane containing the first curvature.

Pre-curved endodontic instrument 10
Chuck 11
Depth calibration grooves 13
Active portion or working length 15
Flutes 17
Cutting edge 19
Central longitudinal axis of 10 21
Apical portion 23
Tip end of 15 and end of 41, 61 25
Engaged portion of 15 27
Unengaged portion of 15 29
Center line of 15 31
First curved portion or curvature 41
Start of 41,51 43

First plane 45
Envelope of motion 47
Second curved portion or curvature 51
Rising or falling sloping portion 52
End of 51, start of 61 53
Second plane 55
Envelope of motion 57
Apex of 51 59
Third curved portion or curvature 61
Rising or falling sloping portion 62
Envelope of motion 67
Apex of 61 69

DETAILED DESCRIPTION OF THE INVENTION

Referring to the figures, a multi-planar pre-curved endodontic instrument 10 made according to this invention includes a chuck 11 configured for insertion into a rotary hand piece, a set of depth calibration grooves 13, and an active portion or working length 15. Working length 15 is typically tapered along its length and includes a plurality of spaced-apart flutes 17 that meet to form either a landed or landless cutting edge 19. The cutting edge 19 provides a desired cutting or scraping effect depending upon the helical angle of the flutes 17, the rake angle at the cutting point of edge 19, and the direction in which instrument 10 is rotated. The length of working length 15 may vary, but it is typically about 16 mm in length. The mass of the working length 15 is sufficient so that instrument 10 may be used in continuous forward or reverse rotation without "winding up" on itself as flute surface or edge 19 cuts or scrapes at a root canal wall.

Endodontic instrument 10 may be made of a nickel-titanium alloy or other type of super-elastic material typically used for endodontic instruments. Unlike prior art endodontic instruments made of super-elastic material, the centerline 31 of working length 15 is not straight in its entirety with respect to the central longitudinal axis 21 (or axis of rotation) of the instrument 10. Rather, the instrument 10 includes two or more curvatures 41, 51, 61 located along the apical portion 23 of the working length 15, with at least two of the curvatures 41, 51 or 61 lying in a different plane 45, 55 than the other. The apical portion 23 extends from about one-third to one-quarter of the working length 15 to the tip end 25. For example, the apical portion 23 of a 16 mm working length 15 extends to about 4 to 5 mm above the tip end 25 of the instrument 10.

The first curvature 41 is located in a first plane 45 and places tip end 25 a distance $\Delta_{1X}$ from the central longitudinal axis 21 of instrument 10 (see FIGS. 9 & 11). For purpose of description, first plane 45 can be a horizontal or X-plane. In one preferred embodiment, endodontic instrument 10 is designed for slight to medium root canal curvatures with curvature 41 being formed by a radius "R" which allows the curve 41 to sweep away from axis 21 at an angle $\alpha$ in a range of about 30-45° (see e.g., FIG. 2). In another preferred embodiment, endodontic instrument 10 is designed for severe root canal curvatures and radius "R" places allows curve 41 to sweep away from axis 21 at an angle $\alpha$ in a range of about 60-75° (see e.g., FIG. 1).

Because the central longitudinal axis 21 serves as the central axis of rotation for instrument 10, the unrestrained envelope of motion 47 provided by curvature 41 at tip 25 is defined by a circle having a diameter $2\Delta_{1X}$ (see FIG. 8). When the first curvature 41 is in a restrained condition, that is, when working length 15 is working its way down a root canal, the envelope of motion 47 may be less than it is in the unrestrained state but still greater than one provided by a typical endodontic instrument having a straight centerline along the apical portion.

Up until the start 43 of curvature 41, the central longitudinal axis 21 and the centerline of working length 15 are common to one another (see FIG. 6). The location of the starting point 43 along the apical portion 23 is determined by the radius "R" and desired angle $\alpha$, with a larger radius R placing the starting point 43 of curve 41 closer to one-third of the working length 15 and a smaller radius R placing the starting point 43 closer to tip end 25. The starting point 43 of the first curvature 41 may also correspond to the starting point of the second curvature 51.

The second curvature 51 is located along a length of the first curvature 41 but lies in a second plane 55 which is different than that of first plane 45 (see FIG. 7). Preferably, the first and second planes 45, 55 are orthogonal planes and, for the purpose of description, second plane 55 is a vertical or Y-plane. Unlike the hook-shaped first curvature 41, which is formed by radius R, the second curvature 51 is a wave-like shape formed by rising and falling sloping portions 52. Each sloping portion 52 may be substantially the same length as the other and arranged at substantially the same angle $\beta$ relative to the central longitudinal axis 21 (see FIG. 7).

The apex 59 of the second curvature 51 places the corresponding point of centerline 31 at a distance $\Delta_{2Y}$ from the central longitudinal axis 21. Because the central longitudinal axis 21 serves as the central axis of rotation for instrument 10, the unrestrained envelope of motion 57 of the instrument 10 provided by second curvature 51 has a diameter equal to that of the diameter of working length 15 at apex 59 plus $\Delta_{2Y \text{ or } 2X}$ (see FIGS. 7 & 8). When the second curvature 51 is in a restrained condition, that is, when working length 15 is working its way down a root canal, the envelope of motion 57 may be less than it is in the unrestrained state but still greater than one provided by a typical endodontic instrument having a straight centerline along the apical portion.

The third curvature 61 preferably starts at the point 53 where second curvature 51 ends and lies on an opposite side of central longitudinal axis 21 (see FIG. 7). The third curvature 61, which has a wave-like shape similar to that of the second curvature 51, preferably lies in the same plane 55 as the second curvature 51. Similar to second curvature 51, third curvature 61 is a wave-like shape formed by rising and falling sloping portions 62. Each sloping portion 62 may be substantially the same length and arranged at substantially the same angle $\gamma$ relative to the central longitudinal axis 21 (see FIG. 7).

The apex 69 of the third curvature 61 places the corresponding point of centerline 31 at a distance $\Delta_{3Y}$ from the central longitudinal axis 21 (see FIG. 8). Because the central longitudinal axis 21 serves as the central axis of rotation for instrument 10, the unrestrained envelope of motion 67 of the instrument 10 provided by third curvature 61 produces an annulus having an outer diameter equal to that of envelope 47 and an inner diameter equal to that of envelope 57.

Generally speaking, any cross-sectional area of the working length 15 which resides within an interior space of a root canal presents a potential contact area for engaging a respective opposing wall of the root canal. The total amount of contact area for the working length 15 is equal to the number of cutting edges 19 in communication with the wall of the root canal multiplied by the contact area of each cutting edge 19. Therefore, the cutting edges 19, which could be landed edges, create drag that reduces the flexibility of file 10 and requires increased torque to overcome. As the amount of required torque increases, so does the probability of file breakage in the root canal.

Figure 4:
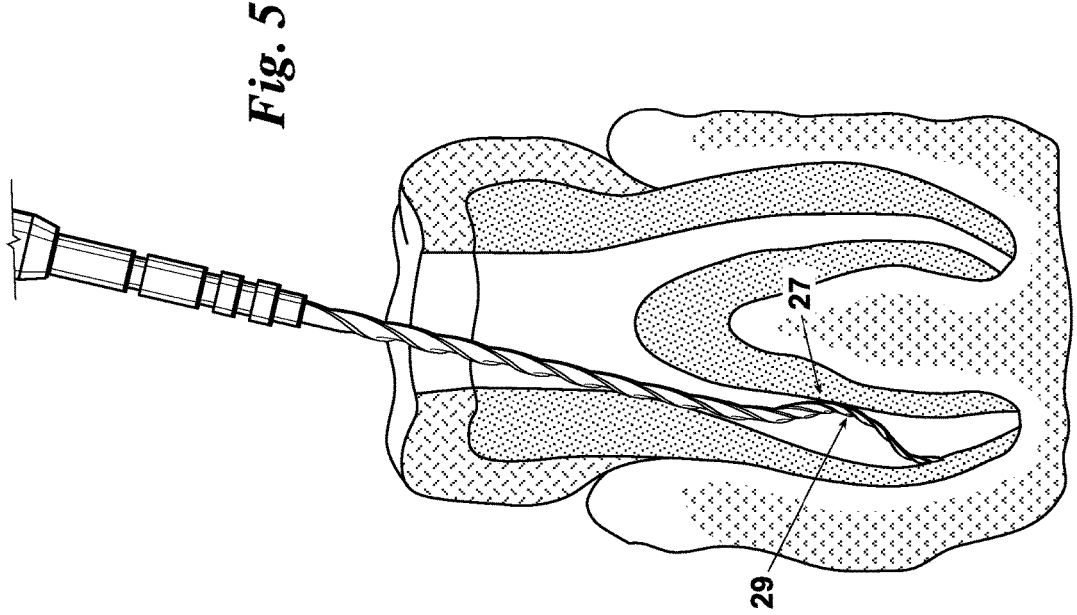
FIG. 4 is view of the file of FIG. 2 as it rotates within a root canal and works its way downward. The pre-curvature of the file prevents a significant portion of the working length of the file from engaging the root canal wall and allows the tip end of the file to continually search the wall. As the file rotates, the tip end of the file makes a circular motion.
Figure 5:
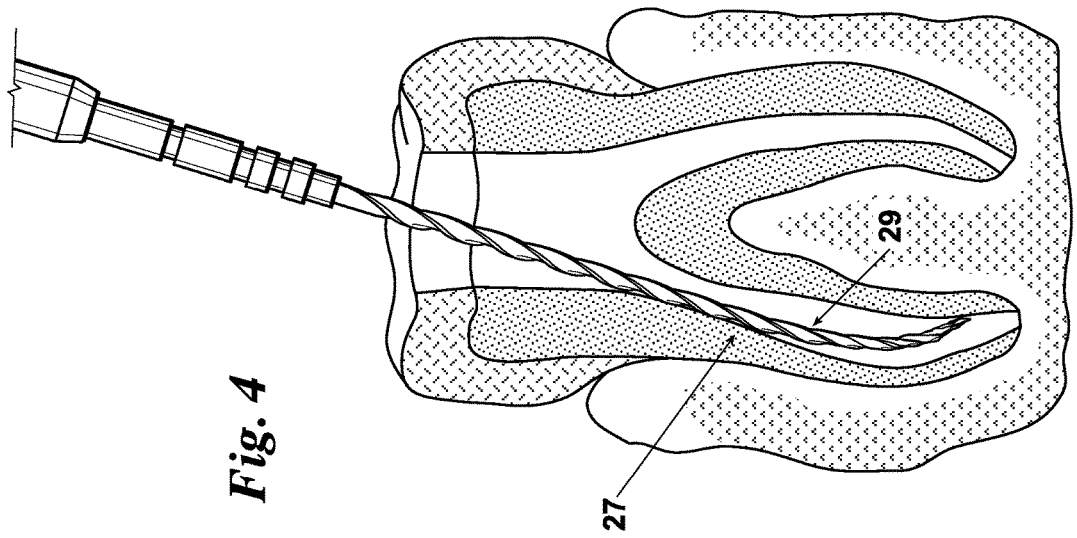
FIG. 5 is a view of a file of FIG. 2 after rotating about 90° from its position as shown in FIG. 4.

Because of its design, endodontic instrument 10 reduces the total amount of contact area between the cutting edges 19 and the root canal as the working length 15 rotates within the root canal and works its way down the root canal. For example, first curvature 41 allows tip end 25 to make a circular motion and search the walls of the root canal (see FIGS. 4 & 5) and enter lateral- and delta-type openings located along the main wall. When the tip end 25 encounters a ledge or irregularity in the wall, the end 25 breaks free of it rather than becoming entrapped or causing the working length 15 to deviate from the curvature of the canal. As tip end 25 continues its search of the wall, the curvatures 41, 51, 61 allow the working length 15 to search the curvature of the canal and place pressure on the working length 15, forcing a portion 27 of the working length 15 toward an inside of the root canal and another portion 29 toward an outside of the canal (see FIGS. 7 & 12). In other words, whatever portion of the root canal wall that tip end 25 encounters, portion 29 is forced to the opposite wall.

This forced-inside, forced-outside action provides for cleaning and enlarging of the root canal as working length 15 works its way down the root canal. A straight file, even if formed from a superelastic material, always follows the outside of the curve. Additionally, whenever tip end 25 encounters a short radius curve, the tip end 25 and working length 15 easily enter the curve. When a straight file encounters the same curve, it has a tendency to transport the curve. Last, despite having two or more curvatures 41, 51, 61, the apical portion 23 of the working length 15 can straighten when being compressed by tight, straight passageways of the root canal and then reform to its curved shape after emerging from those passageways.

While preferred embodiments of an endodontic file made according to this invention have been disclosed with a certain degree detail, the scope of the invention is limited by the following claims.

What is claimed is:

1. An improvement endodontic instrument configured for use in a rotary hand piece and having a working length made of a shape memory material and including a plurality of flutes forming a cutting edge, the improvement comprising:
   the working length including
      a straight non-apical portion whose central longitudinal axis is a central rotational axis of the endodontic instrument and
      a pre-curved apical portion whose central longitudinal axis does not lie along the central rotational axis of the endodontic instrument,
   the pre-curved apical portion beginning at about one-third to one-quarter of the working length as measured from a tip end of the endodontic instrument and ending at the tip end, the pre-curved apical portion having at least three curvatures including at least one curvature that spirals about the central rotational axis of the endodontic instrument, the at least one curvature having a radius of curvature "R" which places the tip end at an angle in a range of about 300 to 750 relative to the central rotational axis.

2. The improvement according to claim 1, the angle being in a range of about 30° to 45°.

3. The improvement according to claim 1, the angle being in a range of about 60° to 75°.

4. The improvement according to claim 1 further comprising a second curvature lying in a different plane extending left and right of the central rotational axis than that of a plane extending left and right of the central rotational axis and containing the at least one curvature.

5. The improvement according to claim 4 further comprising the different plane being an orthogonal plane relative to the plane containing the at least one curvature.

6. The improvement according to claim 1 further comprising the second curvature lying along a portion of a length of the at least one curvature.

7. The improvement according to claim 1 further comprising a start point of the at least one and second curvatures being the same start point.

8. The improvement according to claim 1 further comprising the second curvature having a sloping portion relative to the central rotational axis.

9. The improvement according to claim 1 further comprising a third curvature lying along a length of the at least one curvature and between an end of the second curvature and a tip end of the working length.

10. The improvement according to claim 9 further comprising the third curvature having a sloping portion relative to the central rotational axis.

11. The improvement according to claim 9 further comprising the third curvature lying in a same plane as the second curvature.

12. An improved endodontic instrument configured for use in a rotary hand piece and having a working length made of a shape memory material and including a plurality of flutes forming a cutting edge, the improvement comprising:
   the working length having a straight non-apical portion whose central longitudinal axis is a central rotational axis of the endodontic instrument and a pre-curved apical portion whose central longitudinal axis does not lie along the central rotational axis, the pre-curved apical portion beginning at about one-third to one-quarter of the working length as measured from a tip end of the endodontic instrument and ending at the tip end and having a first curvature and a second curvature, at least one of the curvatures spiraling about the central rotational axis, the second curvature lying in a different plane extending left and right of the central rotational axis than that of a plane extending left and right of the central rotational axis and containing the first curvature.

13. The improvement according to claim 12 further comprising the different plane being an orthogonal plane relative to the plane containing the first curvature.

14. The improvement according to claim 12 further comprising the second curvature lying along a portion of a length of the first curvature.

15. The improvement according to claim 12 further comprising a start point of the first and second curvatures being the same start point.

16. The improvement according to claim 12 further comprising a third curvature lying along a length of the first curvature and between an end of the second curvature and a tip end of the working length.

17. The improvement according to claim 16 further comprising the third curvature lying in a same plane as the second curvature.

* * * * *